United States Patent [19]
Klingen et al.

[11] 3,969,623
[45] July 13, 1976

[54] VARIABLE TEMPERATURE FLAT PLATE POWDER DIFFRACTION CAMERA

[75] Inventors: Theodore J. Klingen, Oxford, Miss.; John H. Kindsvater, Reno, Nev.

[73] Assignee: The University of Mississippi, University, Miss.

[22] Filed: Jan. 10, 1975

[21] Appl. No.: 540,219

[52] U.S. Cl. ............................... 250/275; 250/272
[51] Int. Cl.[2] ........................................ G01N 23/20
[58] Field of Search ........................... 250/272, 275

[56] References Cited
UNITED STATES PATENTS

| | | | |
|---|---|---|---|
| 2,543,825 | 3/1951 | Beu et al. | 250/275 |
| 3,626,185 | 12/1971 | Parrish et al. | 250/275 |
| 3,764,809 | 10/1973 | Haas | 250/275 |
| 3,855,469 | 12/1974 | Pluchery et al. | 250/275 |

Primary Examiner—Alfred E. Smith
Assistant Examiner—T. N. Grigsby
Attorney, Agent, or Firm—Laurence, Stokes & Neilan

[57] ABSTRACT

A flat-plate camera for X-ray diffraction studies of powdered materials under various conditions of temperature. A spindle assembly is provided for rotating a sample specimen about the longitudinal axis of the sample and such that the axis of an X-ray beam striking the specimen, orthogonally intersects the longitudinal axis of the specimen. The spindle assembly includes means for providing a temperature controlled air stream which is directed towards the sample specimen along its longitudinal axis for varying the sample temperature. A flat film plate to be exposed is vertically mounted in back of the sample specimen and is asymmetrically arranged with respect to the X-ray beam. An X-ray shield is provided to permit exposure of sequential segments of the film plate thereby providing direct comparison on one photograph of different exposures taken at various sample temperatures.

11 Claims, 4 Drawing Figures

VARIABLE TEMPERATURE FLAT PLATE POWDER DIFFRACTION CAMERA

BACKGROUND OF THE INVENTION

The present invention relates to an apparatus for studying the structure of materials by obtaining X-ray diffraction patterns. More specifically, it is directed towards a novel apparatus for obtaining X-ray diffraction patterns of powdered substances under various conditions of temperature and for continuously following structural changes in the material due to temperature variations.

Many camera apparatus have been designed and used in the past to produce crystallographic data on film using one of the standard diffraction procedures. In this connection, there is known the Debye-Scherrer type of camera in which the specimen of material to be studied is mounted for rotation at the center of a circular cassette in which photographic film is wrapped around the iner wall of the camera. A collimated X-ray beam is then passed through a hole in the film and directed towards the specimen of material which is being continuously rotated. The resulting diffracted X-rays fall upon the cylindrically shaped film as a series of concentric rings. This series of concentric rings is the planar representation of a series of conical surfaces of different opening angles. These conical surfaces are so arranged that they have a common vertex at the source point of the ray and their axis extends in the direction of the primary ray. The opening angle of the conical surface and the intensity of the scattered radiation relative to the resulting diffraction cone are a function of the structure of the specimen of material which produces the diffraction.

The powder method for testing the X-ray diffraction characteristics of various materials is an extremely useful qualitative tool in both physics and chemistry. In the prior art, finely powdered material which is to be studied is drawn into a hollow fiber having a very small internal diameter. The procedure employed for filling the fibers is necessarily of such nature that the material being analyzed is usually maintained at room temperature and exposed to the atmosphere during the filling operation. The material is also exposed to the atmosphere in most conventional diffraction studies during the time that it is subjected to X-rays. On the other hand, X-ray diffraction studies can also be carried out at extremely high temperatures when employing special types of apparatus, which are modifications of the Debye-Scherrer type of camera. It is, however, of considerable interest to be able to detect temporary structural changes uninterruptedly, and to discover changes in the materials which occur upon changes in temperature.

Although a number of variable temperature powder diffraction cameras are known in the prior art, each of these cameras is a modification or an improvement over the Debye-Scherrer geometry. A distinct disadvantage of the Debye-Scherrer type camera in conducting variable temperature studies is the relatively closed geometry of the camera. Cameras utilizing flat-plate recording techniques employ an open geometry and have proved useful for variable temperature studies of materials, particularly of the mesomorphic phase transitions of organic and organometallic compounds wherein only low-angle diffraction lines are observed.

It is, therefore, a primary object of this invention to provide a novel apparatus for conducting X-ray diffraction studies of powdered substances under various conditions of temperature.

It is another object of this invention to provide a continuously recorded diagram of structural changes in materials which occur upon changes in temperature.

It is further an object of this invention to provide a powder diffraction camera in which the setup procedures required to perform variable temperature studies may be conducted without removing the camera from the diffraction unit to which it is attached.

In carrying out these and other objects of the present invention there is disclosed a flat-plate powdered diffraction camera which is suitable for variable temperature studies of powdered materials. The camera of the present invention is mounted on a conventional powder camera track and up to five 1 inch pictures can be taken on each 5 by 7 inch Weissenburg film by moving filmholder to expose segments sequentially, thus presenting side-by-side comparison of structural changes observed during mesomorphic transition in various specimens of material. The filmholder is mounted asymmetrically with respect to the X-ray beam since the sample capillary is near the base of the camera and the film to be exposed is vertically mounted in back of it. Both positive and negative diffraction lines are recorded for low order reflections, and tan $2\theta$ is recorded instead of the normal $2\theta$ angle. Samples of materials to be studied are sealed in evacuated heat resistant glass capillaries and mounted in a rotatable spindle assembly. The axis of the X-ray beam is designed to intersect the longitudinal axis of the sample capillary at right-angles. The temperature of the sample capillary is accurately regulated by directing a temperature controlled air stream, which emanates form the spindle assembly, along the longitudinal axis of the sample.

Additional objects, advantages and features of the present invention reside in the construction, arrangement and combination of parts involved in the preferred embodiment of the invention as will appear from the following description and accompanying drawings wherein.

DESCRIPTION OF THE PREFERRED EMBODIMENT

Figure 1:
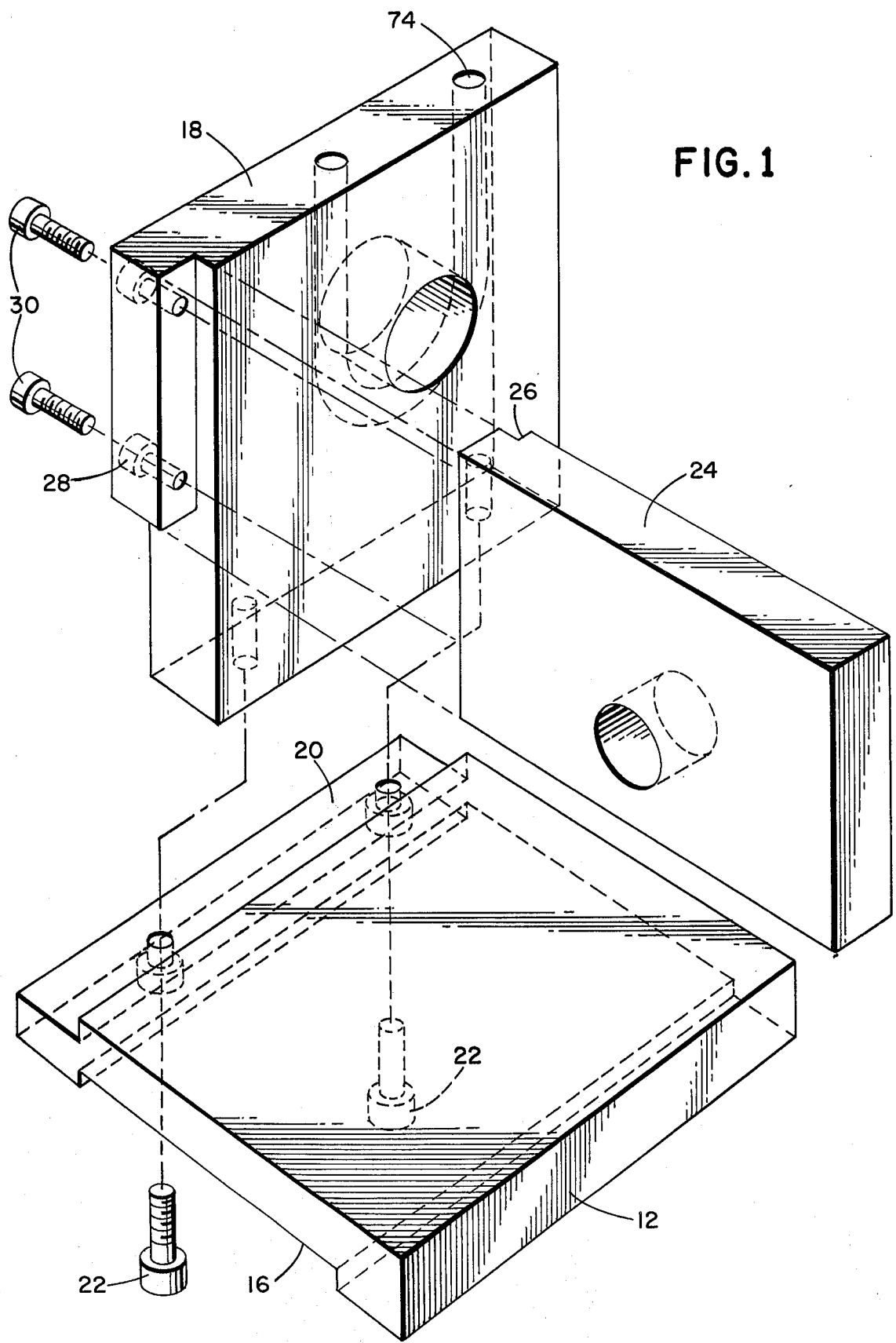
FIG. 1 is an exploded perspective view of the camera of the present invention.
Figure 4:
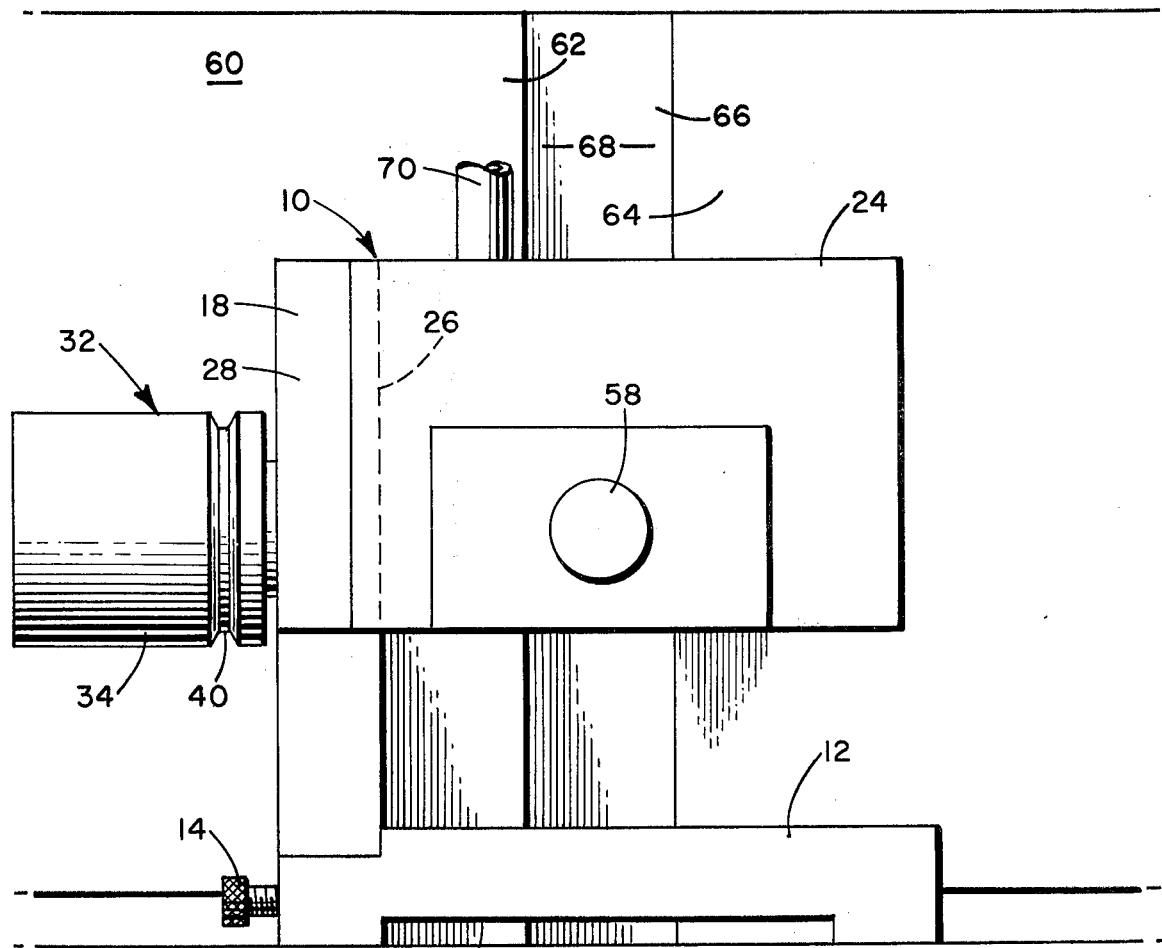
FIG. 4 is a plan view of the camera of FIG. 1.

In the preferred embodiment, the camera 10 is mounted on a standard X-ray camera track (not shown). The track is provided with an adjustment to permit aligning the camera with the X-ray source. A base plate 12 of the camera is fitted onto this track and is horizontally moveable with an adjustment screw 14, which also serves for alignment of the camera with the X-ray source. To facilitate the mounting of the camera 10 on the standard X-ray track, a channel 16 in the base plate 12 is provided, see FIG. 1. Mounted vertically at one end of the base plate 12 is a spindle support or main plate 18. To ensure proper mating of the base plate 12 and the main plate 18, a recess or cut 20, which runs the length of the side edge of the base plate 12 is provided. The width of the cut 20 along the surface of the base plate 12 is identical to the width of the main plate 18. The depth of the recess or cut 20 in the surface of the base plate 12 need only be that which will ensure proper mating of the main plate 18 to the base plate 12 and to provide adequate vertical alignment of the main plate 18 with respect to the camera track. The main plate 18 is secured to the base plate 12 by appropriate screws 22. Secured to the main plate 18 is a third plate or end plate 24. The end plate 24 is mounted perpendicular to the main plate 18, and vertically with respect to the base plate 12. In the preferred embodiment, the rear surface of the end plate 24 and the front surface of the base plate 12 are coplanar. As shown in FIG. 4, the end plate 24 is mounted to the main plate 18 such that there is a space between the bottom surface of the end plate 24 and the top surface of the base plate 12. As with the base plate 12, a recess or cut 26 is provided in the edge surface of the end plate 24 for mating with the main plate 18. An appropriate counterpart 28 to the cut 26 is provided on the main plate 18 for added stability and to ensure proper alignment of the end plate 24 with the main plate 18 and the base plate 12. The end plate 24 is secured to the main plate 18 by appropriate screws 30.

In the preferred embodiment, the base plate 12, the main plate 18 and the end plate 24 are fabricated from aluminum, however, any other suitable material can be employed.

Figure 3:
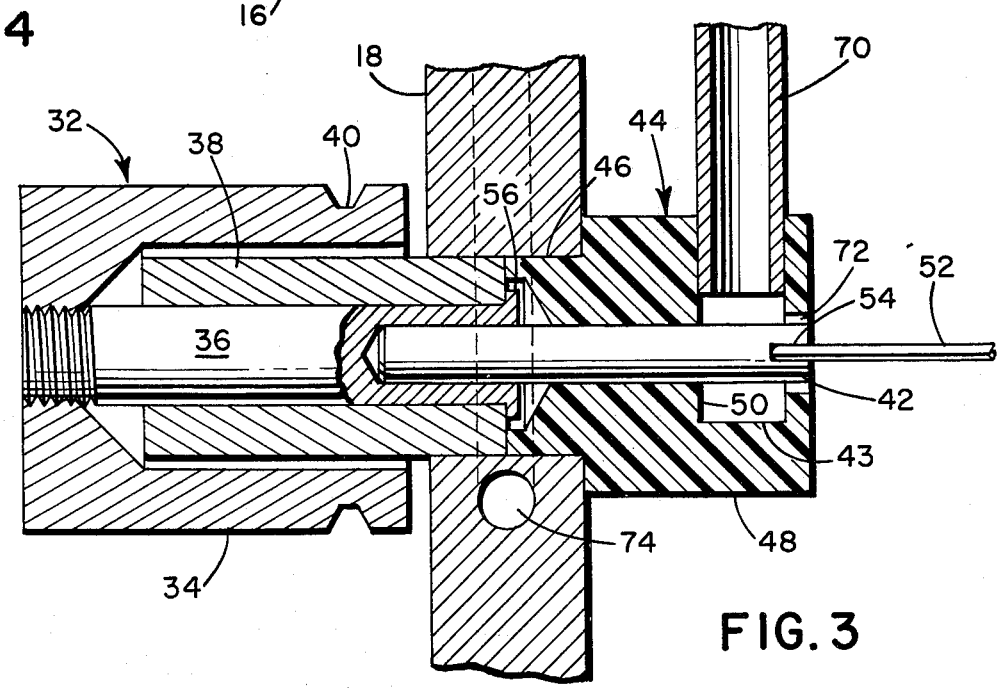
FIG. 3 is a cross-sectional view of a spindle assembly of the camera of the present invention.

The material sample to be photographed is sealed in a conventional manner in evacuated glass capillaries 52 and mounted in a rotating spindle assembly 32, which in turn is supported by the main plate 18, see FIG. 3. The spindle assembly 32 includes a pulley wheel 34 to which a shaft 36 is threaded. The pulley wheel 34 is cylindrical in shape and the longitudinal axis of the wheel 34 is coaxial with that of the shaft 36. Journalled onto the shaft 36 is a long bushing 38, the outer cylindrical surface of which is supported by the main plate 18. In the preferred embodiment, the pulley wheel 34 and shaft 36 are fabricated from aluminum, while the bushing 38 is fabricated from bronze. Again, any other suitable material may be substituted for these elements. The pulley wheel 34 is provided with a V-shaped groove 40 in which a suitable endless belt is mounted. To provide rotating motion to the shaft 36, the endless belt is also mounted onto the shaft of a motor (not shown), in the conventional manner. In view of the torque which will be transmitted to the shaft 36 by rotating the pulley wheel 34, the bushing 38 is designed to be comparatively long to provide an adequate bearing surface for the shaft 36. In addition, this arrangement will ensure that the spindle assembly shaft 36 rotates accurately about its own axis without any side play.

Secured to the shaft 36 is a teflon sample holder 42. This sample holder 42 is an extension of shaft 36 and is coaxial therewith. In the preferred embodiment, teflon was selected as the material from which to fabricate the sample holder 42 because of its good thermal characteristics, however, other suitable materials may be utilized. The sample holder 42 is of smaller diameter than that of the shaft 36 and is secured in a cavity in the non-threaded end of the shaft 36 by cement or other suitable heat insulating material. Bushing 44 has a first portion 46 having an outside diameter identical with that of the bushing 38, and a second portion 48 having an outside diameter slightly larger than that of the first portion 46. The first portion 46 is supported by the main plate 18, while the cylindrical surface of the second portion 48 is completely exposed. The unsecured end of the sample holder 42 is flush with the exposed end of the second portion 48 of the bakelite bushing 44. A cylindrical cavity 50 having a longitudinal axis perpendicular to and coplanar with the axis of the sample holder 42 is provided near the exposed end of the second portion 48 of the bakelite bushing 44. The depth of the cylindrical cavity 50 in the bushing 44 is such that an air passage exists between the cylindrical surface of the sample holder 42 and the base 43 of the cylindrical cavity 50. The diameter of the cavity is slightly larger than that of the sample holder 42 to permit air circulation around the cylindrical surface of the sample holder 42 within the cavity 50. To provide an air passage 72 from the cavity 50 along the cylindrical surface of the sample holder 42 to the exposed end cross-sectional surface of the second portion 48 of the bakelite bushing 44, the inside diameter of the segment of the second portion 48 of the bushing 44 between the cylindrical wall of the cavity 50 and the exposed end cross-sectional surface of the bushing 44 is made slightly larger than the diameter of sample holder 42. The air passage 72 is parallel to the longitudinal axis of the sample holder 42. The function of this air passage 72 will become apparent later.

Sample capillaries 52 are mounted to the spindle assembly 32 by inserting an end of the sample capillary 52 into a slot 54 which is provided in the tip of the sample holder 42. The purpose of the slot 54 is to permit sample capillaries to be positioned properly in the path of the X-ray beam, both vertical and horizontal adjustments being easily made. Modeling clay or other suitable material can be used to hold the sample capillary 52 in the slot 54.

As briefly discussed earlier, the spindle assembly 32 is mounted to the main plate 18. More specifically, an aperture having a diameter substantially identical with that of the outside diameter of the bronze brushing 38 is provided in the main plate 18. To mount the spindle assembly 32 onto the main plate 18, the aluminum shaft 36 and the sample holder shaft 42 are assembled. The bronze bushing 38 and the bakelite bushing 44 are then journalled onto this shaft assembly. To prevent the bronze bushing 38 from moving longitudinally along the shaft 36 onto the smaller diameter shaft of the sample holder 42, a lip or flange 56 is provided at the unthreaded end of the aluminum shaft 36. This shaft assembly along with the respective bushings is then inserted through the aperture provided in the main plate 18 until the larger diameter second portion 48 of the bakelite bushing 44 prevents further travel. The pulley wheel 34 is then threaded onto the shaft 36 and an appropriate endless belt can now be mounted in the V-groove 40. The bushings 38 and 44 only provide a bearing surface for their respective shafts 36 and 42, and only the pulley wheel 34, the aluminum shaft 36 and the sample holder shaft 42 are designed to have freedom of rotation. The bushings 38 and 44 are designed to be rigidly supported by the main plate 18.

Figure 2:
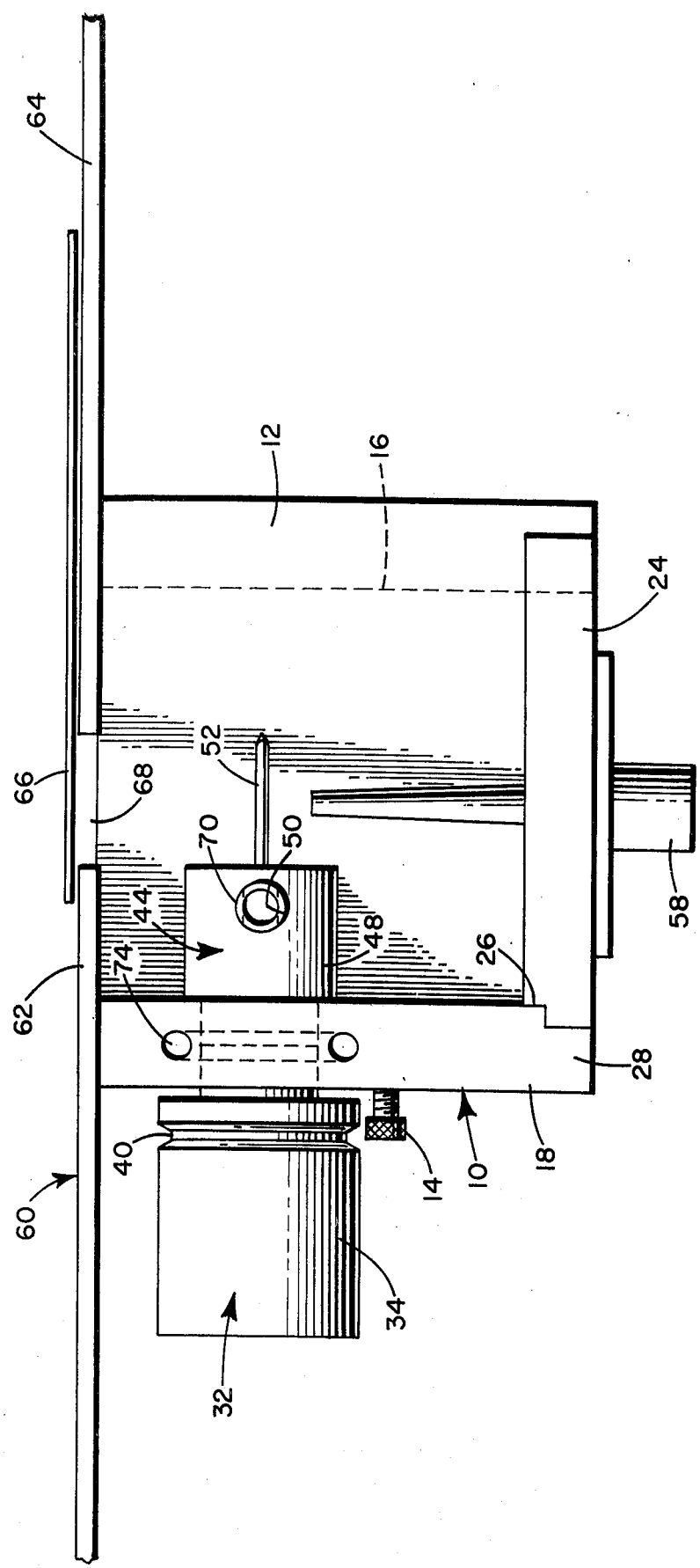
FIG. 2 is a top view of the camera of FIG. 1.

Mounted to the end plate 24 is a standard collimator assembly 58, see FIG. 2. The collimator assembly 58 is aligned so that in operation, the X-rays are introduced through the collimator assembly 58, and engage the material sample capillary 52 to be photographed. The collimator assembly 58 is positioned so that the axis of the X-ray beam will intersect and be normal to the longitudinal axis of the spindle assembly 32.

In the preferred embodiment, a 5 by 7 inch Weissenberg film is employed. Thus, up to five 1 inch pictures can be taken on each 5 by 7 inch Weissenberg film by moving a film holder (not shown) to expose segments sequentially. As a result, side-by-side comparison of structural changes observed during mesomorphic transitions can be observed on one film plate. To facilitate and ensure the exposure of only small segments of the flat photographic plate, a shield assembly 60 is provided. The shield assembly 60 is vertically mounted to the base plate 12 by means of appropriate screws (not shown). The plane of the shield assembly 60 is parallel to the plane of the end plate 24 and is perpendicular to the axis of the X-ray beam. The shield assembly 60 includes a first shield element 62 and a second shield element 64 such that a spatial opening 68 of only 1 inch exists between the shield elements 62 and 64. The film 66 is mounted on a film holder (not shown) on the back of the shield assembly 60. This film holder rides in a track on the rear of the shield assembly 60, and allows the flat-plate film 66 to be moved 1 inch at a time from left to right exposing 1 inch segments to the spatial opening 68. As is readily apparent from this arrangement, the film 66 is considered to be asymmetric with respect to the X-ray beam, since the sample capillary 52 is near the base of the camera 10 and the film 66 to be exposed is vertically mounted to the rear of the sample capillary 52. The geometry of the flat-plate film 66 will give rise to recording of $\tan 2\theta$ as opposed to the recording of $2\theta$ as in the cylindrical geometry of the prior art powder camera. In addition, both positive and negative diffraction lines are recorded for low order reflections which are used to determine the zero point for the higher reflections. Although $\tan 2\theta$ is recorded instead of the normal $2\theta$ angle scattered from the X-ray beam, slightly more complex data reduction is encountered. These calculations, however, can be easily performed with the aid of existing digital computing facilities. The advantages gained, however, by employing the open geometry of the flat-plate powder camera far outweigh any data calculation difficulty which will be experienced.

To vary the temperature of the sample, the cavity 50 in the second portion 48 of the bakelite bushing 44 is employed. To lower the temperature of the sample to be photographed, a copper tube 70 is secured to the opening of the cavity 50. A cold air stream from a standard evacuated copper transfer tube (not shown) is directed into the tube 70 which in turn directs the air stream along the sample axis via the air passage 72. Comparatively low temperatures can be attained in this manner if the area between the collimator assembly 58, which is mounted on the end plate 24, and the camera shield assembly 60 is enclosed in mylar plastic or other suitable material to prevent ice formation on the sample capillary 52 during exposure. Extremely low temperatures may be attained by employing more elaborate transfer dewars exiting directly on the sample capillary 52. To accurately record temperatures, a Chromel-Alumel thermocouple or other suitable thermocouple can be positioned along the sample axis just below axis of the X-ray beam.

In heating the sample capillary 52 above ambient temperature, the copper tube 70 is removed and replaced by a longer tube (not shown) which is encased with a nichrome heating element. An ambient air stream is then passed through the heated tube to the sample capillary 52 via the cavity 50 and the air passage 72. As is readily apparent, the heated air is directed along the full length of the sample capillary 52 including that portion inserted in the slot 54 of the sample holder 42. This prevents sublimation of the sample out of the X-ray beam area. Heating can be controlled in the conventional manner by adjustment of the current flow through the resistance heating element, and by regulating the rate of air flow in the stream passing through this element. Accurate temperature measurements can be made by employing the same Chromel-Alumel thermocouple discussed above.

To prevent the aluminum shaft 36 of the spindle assembly 32 from binding against the bearing surface of the bronze bushing 38, a U-shaped channel 74 is provided in the main plate 18. The channel 74 encircles the aperture in the main plate 18 supporting the bronze bushing 38, and provides a water cooling loop to prevent the bronze bushing from binding during above ambient operations. The water cooling loop 74 is not employed when operating below ambient temperatures.

Since the flow of air through the air passage 72 is parallel to the movement of the film 66, the film 66 will not be damaged or adversely affected by the heating or cooling of the sample capillary 52. Moreover, because of the relatively open geometry of the camera 10, the film 66 can be easily accessed without disturbing the operation of the heating or cooling portion of the camera, which eliminates setting up the desired test conditions each time the film is changed.

Thus, there has been disclosed an X-ray flat-plate powder diffraction camera which allows direct comparison of X-ray powder diffraction line changes, due to structural changes in the test sample which occur as a function of temperature, to be recorded all on one film. This will enable even the smallest changes to be detected without ambiguity.

While there has been disclosed herein a preferred embodiment, it is to be understood that the preferred embodiment of the present invention as shown and described is to be regarded as illustrative only and that the invention is susceptible to variations, modifications and changes within the scope of the appended claims.

What is claimed is:

1. A camera including a source of X-ray radiation for obtaining X-ray diffraction photographs of a powder specimen comprising:
   a support assembly having a first and second axis, said first axis being transverse to said second axis;
   first means mounted to said support assembly for forming a collimated beam of X-radiation, said collimated beam directed parallel to said first axis;
   second means mounted to said support assembly for mounting a powder specimen having a longitudinal axis thereof set parallel to said second axis, said second means maintaining the specimen in an area for impingement by said collimated beam of X-radiation for producing a plurality of diffracted X-rays;
   a flat-plate photographic film slidably supported in an attitude transverse said first axis and responsive to said diffracted X-rays for recording said diffracted X-rays; and
   a planar shield assembly secured to said support assembly for shielding said photographic film from a portion of said diffracted X-rays, said planar shield assembly permitting at least recording of said diffracted X-rays about the intersection of said first axis and said film.

2. The camera of claim 1 wherein said support assembly includes a first rectangular member, a second rectangular member and a third rectangular member; a first end of said second member being orthogonally secured to one end of said first member; a first end of said third member being orthogonally secured to a portion of a second end of said second member; a third end of said second member parallel to said first end of said second member being coplanar with a second end of said third member; said first and third members projecting in the same direction from said second member.

3. The camera of claim 2 wherein said second member includes means for mounting said second means and said third member includes means for mounting said first means.

4. The camera of claim 2 wherein said planar shield assembly is orthogonally secured to a second end of said first rectangular member; said second end of said first rectangular member being adjacent said one end of said first member.

5. The camera of claim 4 wherein said planar shield assembly includes a pair of substantially identical rectangular plates; said plates being coplanar and having their longitudinal axis transverse to said second axis and equidistantly displaced from said first axis; said plates forming a non-contiguous surface.

6. The camera of claim 1 wherein said second means includes means for directing a temperature controlled air stream along the longitudinal axis of the powder specimen.

7. The camera of claim 3 wherein said second means comprises:
a shaft assembly;
means secured to one end of said shaft assembly for receiving rotating motion; and
a bushing assembly for said shaft assembly; said bushing assembly being secured to said means for mounting said second means.

8. The camera of claim 7 wherein said bushing assembly comprises:
a first bushing of uniform outside diameter; and
a second bushing having a first portion and a second portion; said first portion having an outside diameter substantially identical with said outside diameter of said first bushing; said second portion having an outside diameter substantially larger than said outside diameter of said first bushing.

9. The camera of claim 8 wherein said second portion of said bushing assembly includes a cylindrical cavity; said cylindrical cavity having a longitudinal axis transverse to and coplanar with the longitudinal axis of said shaft assembly; said cavity having a diameter larger than the diameter of said shaft assembly; said bushing assembly having a first inside diameter substantially identical to the diameter of said shaft assembly and a second inside diameter larger than said first inside diameter; said second inside diameter of said bushing assembly extending from said longitudinal axis of said cylindrical cavity to the other end of said shaft assembly.

10. The camera of claim 9 wherein a temperature controlled air stream is directed into said cylindrical cavity.

11. The camera of claim 7 wherein said shaft assembly includes means for receiving said powder specimen in the other end of said shaft assembly.

* * * * *